United States Patent [19]

Schaefer et al.

[11] Patent Number: 5,566,626
[45] Date of Patent: Oct. 22, 1996

[54] INCINERATION KILN DEVICES AND METHODS OF PROTECTING THE SAME

[75] Inventors: Walter R. Schaefer, Cherry Hill, N.J.; Eustathios Vassiliou, Newark, Del.; Bruno R. Kuhn, Nassau Bay, Tex.; Joseph F. Guinto, Pitman, N.J.

[73] Assignee: Rollins Environmental Services, Inc., Wilmington, Del.

[21] Appl. No.: 353,670

[22] Filed: Dec. 12, 1994

[51] Int. Cl.⁶ .................................. A47J 36/00
[52] U.S. Cl. .................. 110/246; 432/103; 73/86; 266/99; 266/100
[58] Field of Search ............... 110/246; 432/103, 432/118, 119; 73/86; 266/99, 100

[56] References Cited

U.S. PATENT DOCUMENTS

| | | | |
|---|---|---|---|
| 1,579,030 | 3/1926 | Rank et al. | 432/119 |
| 1,972,728 | 9/1934 | Andrus | 73/86 |
| 2,633,347 | 3/1953 | Heyman | 432/119 |
| 3,078,707 | 2/1963 | Weaver | 73/86 |
| 3,430,393 | 3/1969 | Landes et al. | 52/105 |
| 3,829,877 | 8/1974 | Davis | 263/33 |
| 4,022,572 | 5/1977 | Klein et al. | 432/214 |
| 4,103,539 | 8/1978 | Worley | 73/86 |
| 4,253,408 | 3/1981 | Kramer | 110/346 |
| 4,269,397 | 5/1981 | Strimple et al. | 266/44 |
| 4,473,379 | 9/1984 | Liu | 48/210 |
| 4,846,083 | 7/1989 | Serbent | 110/344 |
| 4,953,481 | 9/1990 | Clayton | 110/342 |
| 5,228,398 | 7/1993 | Byerly et al. | 110/246 |
| 5,301,621 | 4/1994 | Vassiliou et al. | 110/346 |
| 5,353,722 | 10/1994 | Vassiliou et al. | 110/346 |

FOREIGN PATENT DOCUMENTS 2605409  4/1988  France ........................ 73/86

*Primary Examiner*—Thomas E. Denion
*Attorney, Agent, or Firm*—E. Vassiliou

[57] ABSTRACT

An incineration kiln of the slagging mode, which has an outer shell and a protective layer inside the shell with quantum failure identifiers. The quantum failure identifiers recognizes one or more stages of increasing degree of failure of the protective layer, so that an operator may be warned and take suitable measures to protect further deterioration of the protective layer and restore the same.

19 Claims, 7 Drawing Sheets

INCINERATION KILN DEVICES AND METHODS OF PROTECTING THE SAME

FIELD OF THE INVENTION

The present invention pertains to kilns, especially of the slagging type, which comprise an outer metal shell protected by an inside refractory layer, and methods of protecting said kilns.

BACKGROUND OF THE INVENTION

Incinerator kilns, and especially those of the rotary type, have an outside metallic shell, usually steel, the inside of which is fully covered by a thick ceramic or refractory, usually in the form of fire bricks having a total thickness exceeding in many cases 25 cm. These kilns usually operate at a exit gas or off-gas temperature in the range of about 1,600° to 2,400° F. The ceramic or refractory walls, however, are very vulnerable to erosion and corrosion, due to the hostile conditions created by the nature of incinerated materials and high temperatures, especially, if alkali metals are present.

If the viscosity of slag in the kiln is adequately high, it may form a rather thick viscous coating on the refractory and thus protect it from the hostile environment. However, when the viscosity of the slag is very low, the slag contributes to the erosion and corrosion of the ceramic, both chemically because it serves as a solvent and mechanically, as it allows foreign big pieces of abrasive material to act against the ceramic walls. If the slag is viscous to the point of becoming substantially solid, or if it has never been formed as a liquid, it becomes ineffective in promoting combustion of organic matter, and also in capturing toxic heavy metals. Therefore, it is imperative that the viscosity of the slag is very carefully monitored and controlled within a range of values. Thus, one of the objects of this invention is to control the viscosity of the slag in incinerating kilns.

U.S. Pat. No. 5,301,621 (Vassiliou et al.), which is incorporated herein by reference, describes methods and devices for slag viscosity detection through image analysis of dripping slag within rotary incineration kilns.

U.S. Pat. No. 5,228,398 (Byerly et al.), which is also incorporated herein by reference, describes methods and devices for controlling rotary incineration kilns by determining the position of the kiln outlet at which the slag is exiting.

U.S. Pat. No. 5,353,722 (Vassiliou et al.), which is also incorporated herein by reference, describes preventive slag-viscosity control by detection of alkali metals in the off-gases.

U.S. Pat. No. 4,953,481 (Clayton) discloses the use of melting point enhancers to control slag build-up in garbage, medical waste and sludge incinerators. It is directed to method of modifying the nature of low melting non-combustible components of garbage, medical waste and sludge by the addition of very high melting point metallic compounds so as to render the low melting point materials non adherent or less adherent and easier to remove from furnace surfaces.

U.S. Pat. No. 4,846,083 (Serbent) discloses the production of a product which can be dumped or utilized. The mineral are subjected to a thermal treatment in a rotary kiln, at a temperature at which the charge of the rotary kiln is transformed to a pasty or liquid slag phase. The composition of the charge is so selected that a slag phase is produced in which the main components, which constitute a matrix, are in the range from 60 to 72% $SiO_2$, 10 to 30% $Al_2O_3$, and 5 to 25% CaO+MgO, of said matrix, wherein the total percentage of $SiO_2$+$Al_2O_3$+CaO+MgO equals 100, the total of the main components $SiO_2$, $Al_2O_3$, CaO, and MgO amounts to more than 60% on dry and ignition loss-free basis, of the mineral matter which is charged to the rotary kiln. The slag Phase discharged from the rotary kiln is cooled and the exhaust gas from the rotary kiln is purified.

U.S. Pat. No. 4,473,379 (Liu) discloses improvement of the performance of a slagging coal gasifier by injecting finely divided particles of non-corrosive slag-like solid material into the gasifier near the zone of combustion at a rate at which heat-protective layers of solidified slag are maintained between that zone and metallic materials located near that zone.

U.S. Pat. No. 4,253,408 (Kramer) discloses a method of preventing corrosion of incinerators designed to burn sewage consisting essentially of from about 90 to 98 percent water and from about 2 to 10 percent waste solids by increasing the fusion temperature range of the ash product above the operating temperature of the interior surfaces of the incinerator. The sewage is mixed with additive materials selected from the group $SiO_2$, CaO, $Al_2O_3$, and MgO wherein the CaO, $Al_2O_3$, and MgO are selected from within the range of 10 to 30 percent of the weight of the waste solid sand the $SiO_2$ is selected from within the range of 25 to 30 percent of the weight of the waste solids. Thereafter, the sewage additive mixtures are injected or otherwise dispersed into the combustion zone of an incinerator such that the waste solids and additive particles remain in contact therein for sufficient time for the additives to chemically combine with sewage solids and form combustion products having fusion temperatures ranges above the operating temperatures of the incinerator surfaces.

U.S. Pat. No. 3,340,393 (Landes et al.) discloses a machine with lining bricks which have a face exposed to wear and side and end surfaces which equal the thickness of the bricks and are concealed by adjacent bricks, said thickness defining surfaces having applied thereto wear indicating means. Said means comprise a right angle triangular design in which one of the right angle edges is perpendicular to the exposed face of the brick and located at a distance from the adjacent parallel edge of the thickness defining surface to which the design is applied, the other of its right angle side edges being coincident with and visible at the exposed face of the brick, both said side edges being equal in length to the thickness of the brick. The length of the visible edge of the triangular design changes progressively as the exposed face becomes worn and at all times equals the thickness of the brick.

U.S. Pat. No. 2,289,877 (Davis) discloses refractory lining for rotary kilns, and refractory members useful for forming such lining, as well as processes for making the same.

SUMMARY OF THE INVENTION

The present invention pertains to kilns of the slagging type, which comprise an outer metal shell protected by an inside refractory layer, and methods of protecting said kilns. The protection of the kilns is accomplished by incorporation of special identifiers in the protective layer, which are adaptable to detect deterioration of said protective layer and warn an operator to take appropriate measures for preventing any further failure and/or restore the integrity of the protective layer.

More particularly, this invention pertains to an incineration kiln device of the slagging type comprising:

an outer metal shell having an inside surface and an outside surface;

a protective layer on the inside surface of the outer shell; and a quantum failure identifier at least partially encased within the protective layer.

Preferably, the protective layer comprises a first sub-layer adjacent to the inside surface of the incineration kiln, and a second sub-layer on top of the first sub-layer, and more preferably the first sub-layer comprises modular refractory.

The quantum failure identifier may be encased in the modular refractory or it may be encased in the second sub-layer.

The quantum failure identifier may be a radioactive material, which is preferably non-volatile. In such a case, it is preferably encased in the modular refractory first sub-layer.

The quantum failure identifier, when encased in the second sub-layer, may be in the form of discrete pieces dispersed preferably in a substantially continuous phase, which preferably has a melting point between 2,300° and 3,000° F. It is further preferable that the discrete pieces have a high enough melting point to substantially retain their shape and size for at least 1 hour when subjected to molten slag conditions prevailing during operation of the kiln. Preferably, the average particle size of the discrete pieces is in the range of 0.5 to 4 cm, and more preferably in the range of 1 to 2 cm, which even more preferably have a higher melting point then the melting point of the slag in the kiln, and a lighter color than the slag. The discrete pieces may be selected from the group consisting substantially of gravel, pebbles, china chips and a mixtures thereof.

The quantum failure identifier, may also be encased in the first sub-layer, in the form of discrete pieces dispersed preferably in a granular phase, which preferably has a melting point between 2,300° and 3,000° F. In this case also, it is preferable that the discrete pieces have a high enough melting point to substantially retain their shape and size for at least 1 hour when subjected to molten slag conditions prevailing during operation of the kiln. Preferably, the average particle size of the discrete pieces is in the range of 0.5 to 4 cm, and more preferably in the range of 1 to 2 cm, which even more preferably have a higher melting point then the melting point of the slag in the kiln, and a lighter color than the slag. The discrete pieces may be selected from the group consisting substantially of gravel, pebbles, china chips and a mixtures thereof.

Further, it is preferable that the protective layer also comprises a third sub-layer on top of the second sub-layer consisting substantially of solidified slag, which may be covered by a fourth sub-layer consisting substantially of molten slag.

The present invention also deals with an incineration kiln device of the slagging type comprising:

an outer metal shell having an inside surface and an outside surface;

a protective layer on the inside surface of the outer shell; and a quantum failure identifier at least partially encased within the protective layer;

wherein the protective layer comprises a first sub-layer adjacent to the inside surface of the incineration kiln and a second sub-layer on top of the first sub-layer, the first sub-layer comprising modular refractory, the second sub-layer comprising a substantially continuous phase, the quantum failure identifier being encased in the second sub-layer in the form of discrete pieces dispersed within said substantially continuous phase, the discrete pieces having a high enough melting point to substantially retain their shape and size for at least 1 hour when subjected to molten slag conditions prevailing during operation of the kiln, the average particle size of the quantum failure identifier being in the range of 0.5 to 4 cm; and the protective layer further comprises a third sub-layer on top of the second sub-layer consisting substantially of solidified slag, and a fourth sub-layer on top of the third sub-layer consisting substantially of molten slag.

The instant invention also pertains an incineration kiln device of the slagging type comprising:

an outer metal shell having an inside surface and an outside surface;

a protective layer on the inside surface of the outer shell; and a quantum failure identifier at least partially encased within the protective layer;

wherein the protective layer comprises a first sub-layer adjacent to the inside surface of the incineration kiln and a second sub-layer on top of the first sub-layer, the first sub-layer comprising modular refractory, the second sub-layer comprising a substantially granular phase, the quantum failure identifier being encased in the first sub-layer in the form of discrete pieces dispersed within said substantially granular phase, the discrete pieces having a high enough melting point to substantially retain their shape and size for at least 1 hour when subjected to molten slag conditions prevailing during operation of the kiln, the average particle size of the quantum failure identifier being in the range of 0.5 to 4 cm; and the protective layer further comprises a third sub-layer on top of the second sub-layer consisting substantially of solidified slag, and a fourth sub-layer on top of the third sub-layer consisting substantially of molten slag.

The device of the instant invention may further comprise a monitor outside the outer metal shell, and have the quantum failure identifier in the form of a plurality of electrical conductors encased in the first sub-layer and communicating with said monitor.

The electrical conductors are in the form of wires or in the form of a printed circuit. The conductors preferably form U-loops, which more preferably are arranged to have increasing lengths.

The present invention, also pertains to a method of protecting the integrity of an incineration kiln of the slagging type, the kiln comprising an outer metal shell having an inside surface and an outside surface, and a protective layer on the inside surface of the outer metal shell; and the method comprising the steps of encasing a quantum failure identifier at least partially within the protective layer, slagging the kiln, monitoring the quantum failure identifier during operation of the kiln to detect at least partial failure of the protective layer, and taking corrective action to restore the protective layer.

BRIEF DESCRIPTION OF THE DRAWING

The reader's understanding of this invention will be enhanced by reference to the following detailed description taken in combination with the drawing figures, wherein.

DETAILED DESCRIPTION OF THE INVENTION

As aforementioned, the present invention pertains to kilns of the slagging type, which comprise an outer metal shell protected by an inside refractory layer, and methods of protecting the kilns. The protection of the kilns is accomplished by incorporation of special quantum failure identifiers in the protective layer, which are adaptable to detect deterioration of said protective layer and warn an operator to take appropriate measures for preventing any further failure and/or restore the integrity of the protective layer.

Figure 1:
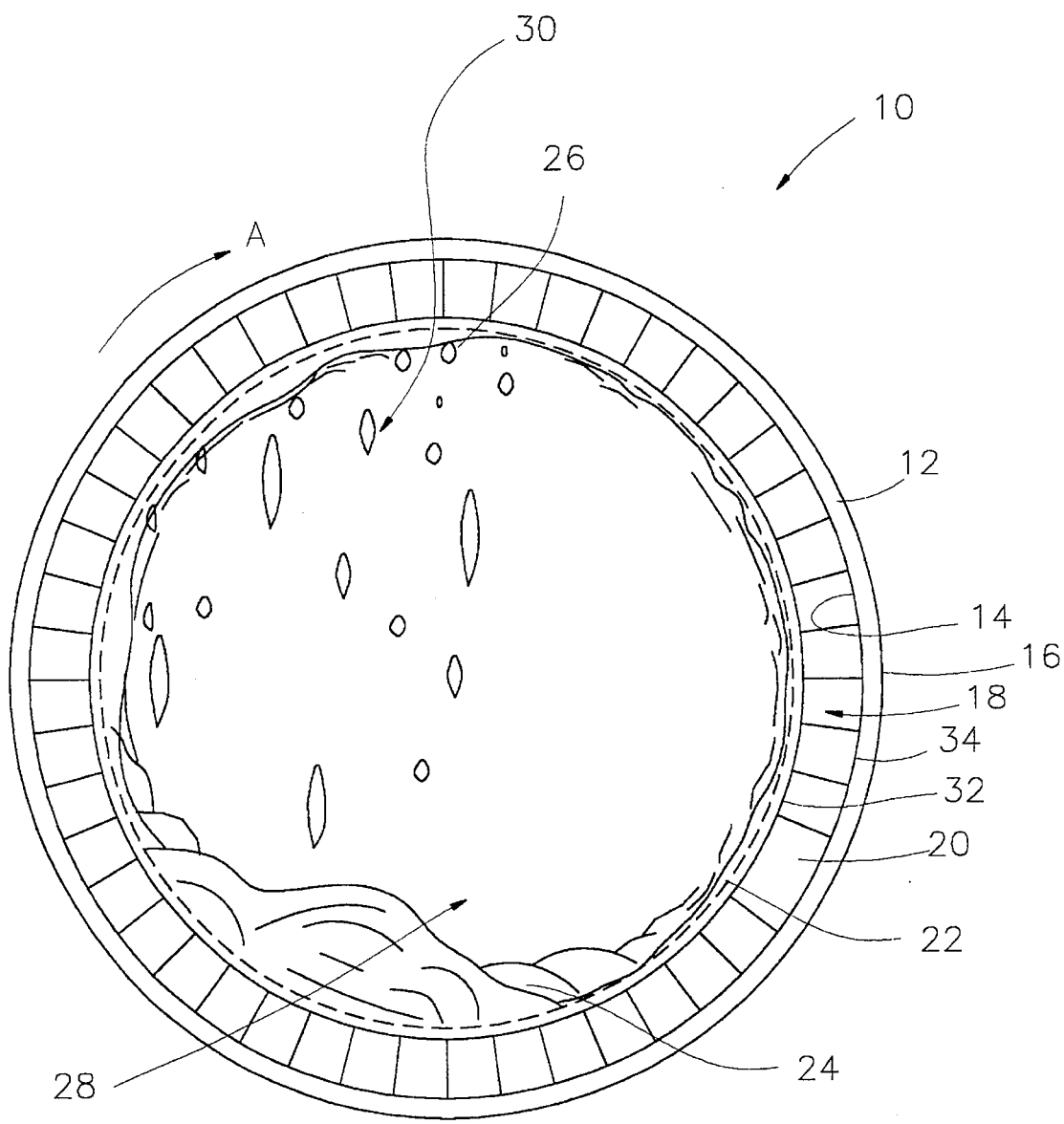
FIG. 1 shows a schematic cross sectional view of a kiln lacking the benefits of the instant invention.

Referring now to FIG. 1, there is depicted a cross sectional view of a conventional rotary slagging incineration kiln 10, which comprises an outer metal shell 12. The outer metal shell 12 is preferably made of steel, and it has an inside surface 14 and an outside surface 16. The kiln 10 also comprises a protective layer 18 disposed on the inside surface 14 of the outer shell 12.

The protective layer 18 is usually made of modular refractory material, such as appropriately shaped individual ceramic bricks, for example, well known to the art of rotary kiln incinerators. This modular protective layer may incorporate one or more layers of refractory bricks. Usually, it comprises a rather thin layer (not shown for purposes of clarity) having a thickness of 2–5 inches, which is used mainly for thermal insulation purposes and it is disposed substantially directly on the inside surface 14 of the outer shell 12. A chemically protective layer is disposed on the thermally insulating layer, having usually a thickness of 8–12 inches. These two or even more layers are included in the protective layer 18, and they are represented by the simple lining of the refractory layer 20 for purposes of simplicity.

In optimal operation of the kiln 10, the protective layer 18 also includes a layer of solidified slag 22, on which a layer of molten slag 24 flows in the direction of kiln rotation A, and falls back from the top of the kiln 26 toward the bottom of the kiln 28 in a form of large drippings 30, as described in detail in U.S. Pat. No. 5,301,621. the existence of the solidified slag layer 22 is important to reduce or prevent attack of the refractory layer 20. However, the solid consistency of the layer 22 is destroyed many times, usually by melting and joining with the molten slag 24, especially when the composition and/or temperature of the molten slag layer 24 are such as to cause excessive reduction in the viscosity of the molten slag layer 24. In such occasions, the combined layers 22 and 24 start attacking chemically the refractory layer 20, especially in the presence of alkali metal moieties. At the same time, erosion of the refractory also takes place, since different types of solids in the kiln are free to abrade the refractory through the combined low viscosity slag layers 22 and 24, the thickness of which is also necessarily reduced due to said low viscosity. These ailments, if allowed to go unobserved and/or not corrected for a period of time may cause serious damage to the kiln.

Although great care is taken to avoid situations of low slag viscosity and of disappearance of the solid slag layer 22, the occurrence of low slag viscosity instances is unavoidable, due to the variability and the compositional unpredictability of the solid waste streams, especially in batch feeding in the form of drums, and the like.

It is also extremely difficult, if not impossible, to judge the degree of damage to the refractory with time, unless such damage is catastrophic or near catastrophic, such as falling off of whole bricks or series of bricks, for example. Even if the viscosity of the slag becomes unwillingly so low as to substantially cause the slag to flow out of the kiln, which kiln is nominally inclined as well known to the art, and reveal the inner face 32 of the refractory 20 positioned toward the center of the kiln 10, judgement of degree of refractory thickness loss is for all practical purposes impossible. The observed faint outline of individual bricks in such a case does not lend itself to an accurate enough dimensional uniformity to allow an observer to optically measure the dimensions of the face of a corroded/eroded brick and after comparing them with the small dimensional differences between the inner face 32 and outer face 34 of a similar individual intact refractory brick, be able to calculate the degree of damage.

In addition, other optical methods such as the one proposed by Landes et al. in U.S. Pat. No. 3,430,393 cannot be used, since the kiln conditions including high temperature and the existence of a layer of slag on top of the refractory, regardless of how thin the layer may be, prevents optical reading, especially in the case of a thin insert throughout the thickness of the brick. Further, such inserts are totally objectionable as considerably deteriorating the integrity of the brick, due to their necessarily large dimensions.

Finally, for an operator to conduct an optical reading of the sort described above, the operator should have to subject the kiln to fully undesirable conditions on purpose, such as lowering the viscosity of the slag to unacceptably low levels on purpose, for substantially complete removal of the slag. Such conditions, cause considerable deterioration to the refractory 20 of the kiln 10, and they should be avoided as much as possible. Thus, they should not be caused on purpose for just routine measurements.

Figure 2:
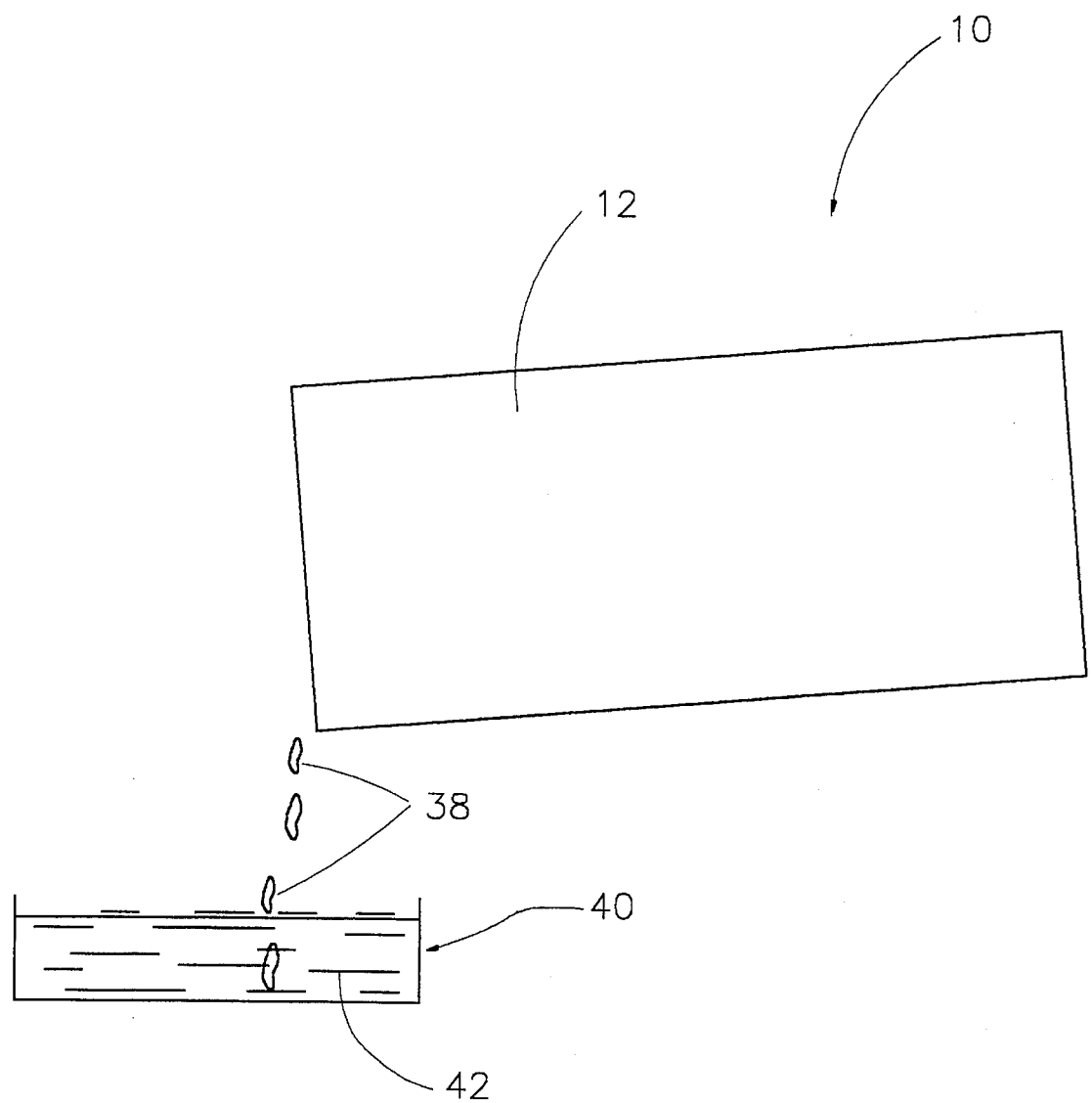
FIG. 2 shows a schematic side view of the kiln of FIG. 1 or of a kiln according to the present invention.

FIG. 2 shows a simplified side view of kiln 10, having the outer shell 12 at an inclined level, with exiting slag 38 falling into deslagger 40, which contains water 42. This arrangement is very well known to the art of incineration, and needs no further explanations.

Figure 3:
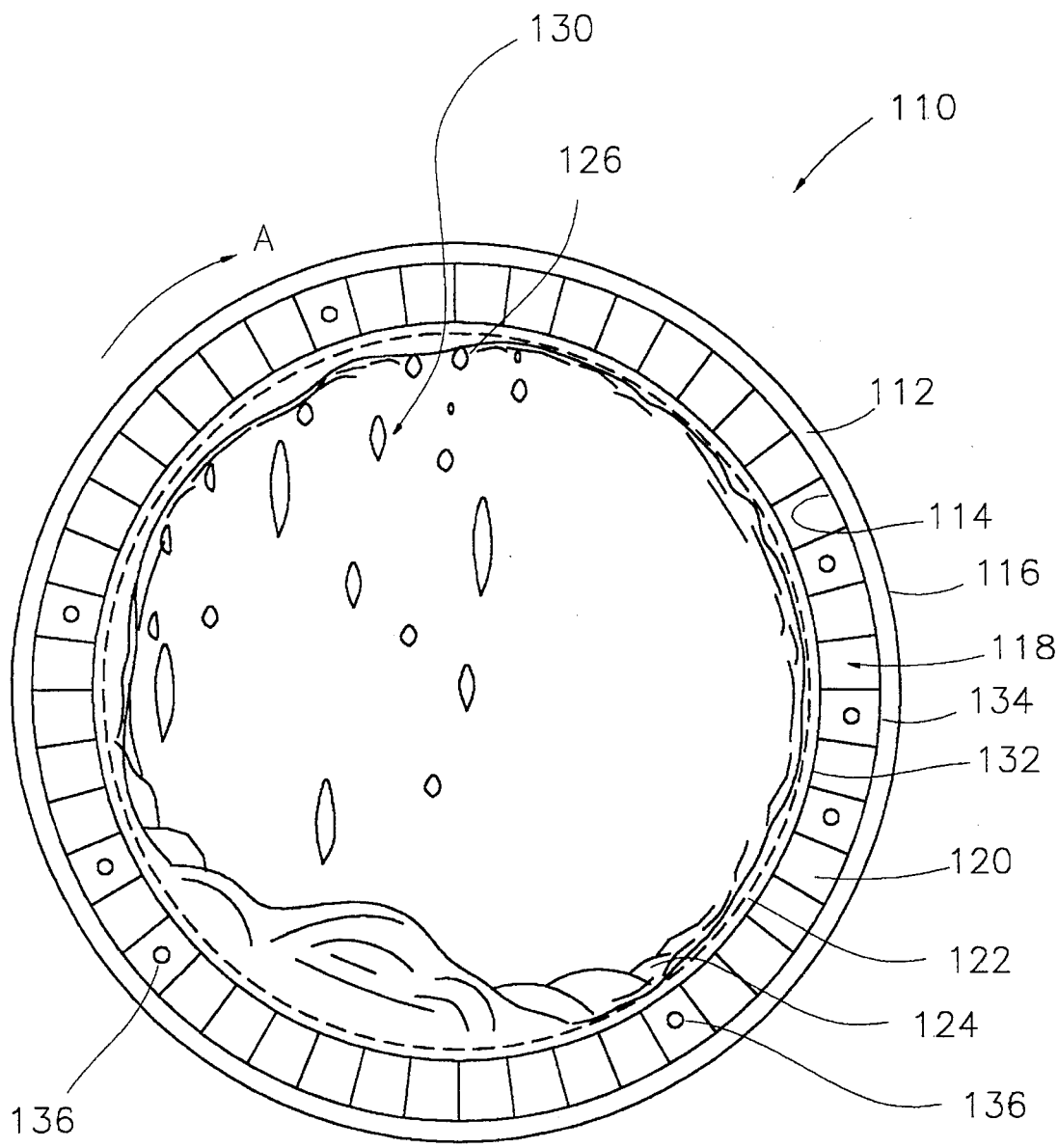
FIG. 3 shows a schematic cross sectional view of a kiln according to a preferred embodiment of the instant invention, wherein quantum failure identifiers are embedded in the modular refractory first sub-layer.

In one embodiment of the present invention, better shown in FIG. 3, there is provided an incineration kiln 110, very similar to the incineration kiln 10 of FIGS. 1 and 2, with the difference that the refractory sub-layer 120, being part of the protective layer 118, contains quantum failure identifiers 136 in at least part of the units (refractory bricks in this case) of the modular sub-layer 120. The quantum failure identifiers are placed within the mass of the refractory bricks, preferably closer to the inner face 132 than the outer face 134 of the modular sub-layer 120. It is preferable that the quantum failure identifiers are categorized to one or more sets. The identifiers belonging to each set should be substantially equidistant from the inner face 134 of the refractory. Only one set of quantum failure identifiers is shown in FIG. 3, all identifiers being substantially equidistant, as compared to each other, from the inner face 134 of the modular refractory sub-layer 120. It is not necessary for each individual brick to have a quantum failure identifier. It is preferable, however, that 1–20% of the bricks contain such an identifier, especially in the case that the identifier is of radioactive nature.

The quantum failure identifiers have been given their name because they are used to detect failure in quanta rather than continuously. For example, in the embodiment shown in FIG. 3, assuming that there is only one set of quantum failure identifiers 136, the detection will take place when the thickness of the refractory brick 120 has decreased to such a degree as to release quantum failure identifiers into the slag, and from there to the deslagger (40 in FIG. 2) as described hereinbelow.

The quantum failure identifiers, according to this embodiment of the instant invention, may be any material in adequate quantity, which has size, shape, and other properties, which allow detection of its presence in the exiting slag (38 in FIG. 2). Examples are materials comprising radioactive elements, preferably non-volatile having low half-life and low radiation levels. Other examples are pebbles or gavel of high melting point, which can withstand the slag and kiln conditions until they are detected in the exiting slag. It is only important that they have such size, shape, and/or other properties, which allow the detection of their presence in the exiting slag, as already mentioned. Common see-shore pebbles, gravel, or pieces of porcelain are examples. It is in most cases critical that these moieties have low adhesion to the refractory brick so that they are released easily into the slag, when the thickness of the brick decreases to the point of exposing them to the slag. The size of the pebbles, or gravel or porcelain pieces, and the like, according to this embodiment of the present invention, is preferably such as to allow them to pass round openings having a diameter of about 5 cm, and be retained by round openings having a diameter of about 3 cm. In the case that radioactive materials are used, the size of the quantum failure identifiers may be considerably smaller, and preferably pebble shaped pieces having an average diameter of 0.5 to 2 cm.

When there are more than one sets of quantum failure identifiers, said identifiers will be released first from the set of identifiers closest to the inner face 132 of the refractory 120. Detection of this set of identifiers in the exiting slag will be interpreted as decrease in thickness of the refractory corresponding to the original position of such identifiers within the refractory brick. The same is true for a second set of identifiers, which will correspond to a second decrease in thickness, and so on.

It is preferable that the one or more sets of quantum failure identifiers are positioned at such distance intervals from each other as to correspond to desirable and critical distances from the inner face 132 of the refractory. For example, if the initial refractory brick thickness is 30 cm, one set at about 6 cm, one set at about 12 cm, and one set at about 20 cm would be desirable to notify the operator of the status of the refractory brick. In an example, where one set is used, it should be preferably placed somewhere around the middle distance between the inner surface 132 and the outer surface 134 of the refractory brick 120. However, the positioning of the identifiers depends on the individual preferences of the operator of the kiln. In some occasions, for example, it might be desirable to place a set of quantum failure identifiers at such a distance from the inner surface 132, that when the thickness of the brick is reduced any further, the brick structure itself would be prone to catastrophic failure by not being able to support itself, due to highly reduced caliper between bricks in a complete circle around the periphery of the kiln.

Depending on the type of the kiln, the type waste it has been designed to incinerate, the feeding mechanism, and other parameters, the major wear may be occurring in only a small zone within the kiln. In such occasions, the identifier set(s) may be placed only in the refractory within such critical small zone.

It is also within the scope of this embodiment to place different types of identifiers in critical different zones, so that differentiation of failure may be made among the critical zones.

In operation of this embodiment, the kiln is made in a manner to comprise refractory layer 120 provided with one or more sets of identifiers, in any manner described above. During the course of the useful life of the kiln, due care is taken to reduce the risk of refractory failure, by controlling the viscosity of the slag, for example, and by using such techniques as described in U.S. Pat. No. 5,301,621 (Vassiliou et al.), 5,228,398 (Byerly et al.), and 5,353,722 (Vassiliou et al.), all of which have been incorporated herein by reference.

Despite of any precautions taken, it is inevitable that the refractory layer will start deteriorating sooner or later, and the time will come that the deterioration will come to a point a point, at which the thickness of the refractory 120 will have been reduced in a manner to expose the identifiers 136, which will be released to the slag and they will be transferred to the deslagger 40 by the exiting slag 38 (FIGS. 2 and 3).

The identifiers are then detected by the operator, either as the slag 38 exits the kiln 10, or in the slag which has fallen into the water 42 of the deslagger 40. If, for example, the identifiers comprise radioactive elements, a Geiger Counter may be used for their detection. If the identifiers are in the form of pebbles, optical inspection of the slag reveals their presence. Since the slag has a generally dark brown or blackish appearance, it is preferable that the quantum failure identifiers are light colored.

Depending on the position of the quantum failure identifiers, when the operator detects them at the exit of the kiln, he or she takes appropriate measures, before catastrophic failure of the protective layer occurs. Such measures may include for example, stopping and realigning the kiln partially or totally to avoid attack of the outer shell 12.

Figure 4:
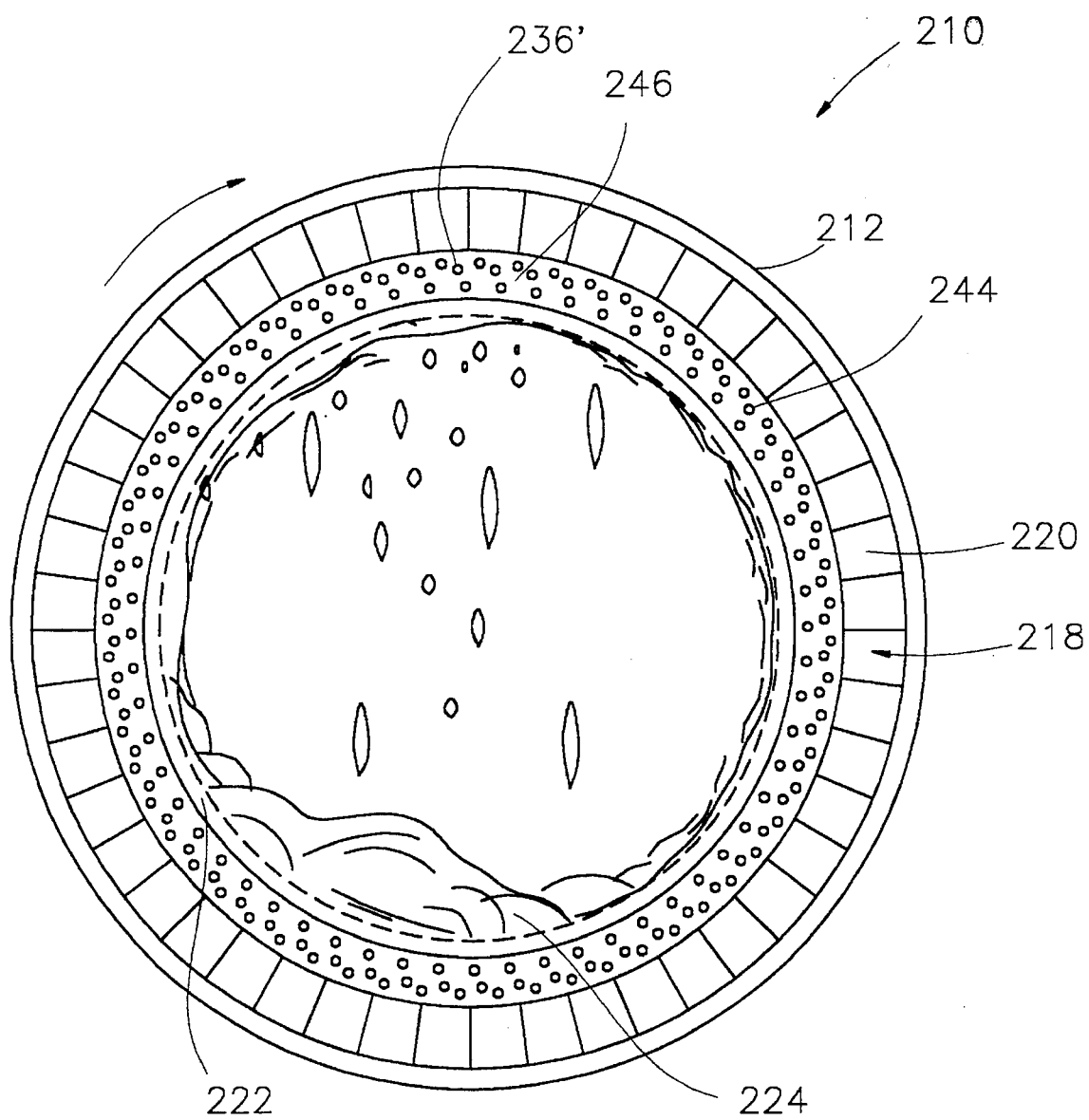
FIG. 4 shows a schematic cross sectional view of a kiln according to a different preferred embodiment of the instant invention, wherein quantum failure identifiers are in the form of discrete pieces are dispersed within a substantially continuous phase in the second sub-layer.

In a different embodiment of the instant invention, better shown in FIG. 4, the protective layer 220 of the kiln 210, in addition to the first modular refractory sub-layer 220, also comprises a second sub-layer 244, in which quantum failure identifiers 236', are encased. The second sub-layer 244 preferably comprises a substantially continuous phase 246, in which there is dispersed discrete pieces of the quantum failure identifier 236'. It is preferable that the substantially continuous phase 246 has a melting point between 2,300° and 3,000° F.

Preferably, the average particle size of the quantum failure identifier 236' is in the range of 0.5 to 4 cm, and more preferably in the range of 1 to 2 cm. It is also preferable that the discrete pieces of the quantum failure identifier 236' have a lighter color than the color of slag exiting the kiln.

The discrete pieces of the quantum failure identifier 236' should have a melting point higher than the melting point of slag 224 used in the kiln 210. It is preferable that they have a high enough melting point to substantially retain their shape and size for at least 1 hour when subjected to molten slag conditions prevailing during operation of the kiln.

The protective layer 218 may further comprise a third sub-layer 222 on top of the second sub-layer 220 consisting substantially of solidified slag, which is covered by a fourth sub-layer 224 consisting substantially of molten slag.

Examples of discrete particles of the quantum failure identifier 236' are gravel, pebbles, porcelain, such as china-chips for example, and the like. One example of the substantially continuous phase is "Black Beauty", which is a by-product of the steel industry, well known to the art, and which comprises silica, alumina and iron oxide. Other aluminosilicate compounds may also be used as the substantially continuous phase 246, as long as they have appropriate melting points as described above.

The construction of a kiln device according to this embodiment is conducted by first lining the kiln with the modular refractory first sub-layer 220 by methods well known to the art. After the modular refractory sub-layer 220 has been properly fired by also well known to the art techniques, the temperature is raised to above the melting point of the material to be used as the continuous phase; for example, between 2,300° and 3,000° F. After the quantum failure identifier has been mixed with the material to be used as the continuous phase, the mixture is fed slowly into the kiln, and the rotational speed of the kiln is adjusted in a manner to form the second sub-layer 244. The temperature is then dropped to a level lower than the melting point of the substantially continuous phase 246, and slag materials, such as glass and sand are fed into the kiln in a similar manner as before. As the thickness of the slag increases, a solid slag third sub-layer 222 is formed, with a fourth sub-layer of molten slag 224 on top of it. The solid slag third sub-layer 222 is formed from the heat losses occurring through the other sub-layers and the outer shell 212.

In operation of this embodiment of the present invention, waste is fed to the kiln, which kiln was prepared as explained hereinabove. Care is taken to maintain the temperature and the feeding such that the solid slag sub-layer does not melt and that the viscosity of the liquid slag is adequately high to prevent such melting of the third sub-layer.

As mentioned in the previous embodiment, despite all attempts to avoid melting of the third sub-layer 222, there will come a time at which sub-layer 222 will melt together with the already molten fourth slag sub-layer 224. One of the reasons that this is not difficult to occur, is that an operator cannot actually see or detect the solid slag third sub-layer 222. The operator can only estimate its presence by the appearance of the liquid slag fourth sub-layer 224.

Thus, if the melting occurred, and the second sub-layer 244 were absent, the molten slag would come into intimate contact with the modular refractory first sub-layer 220, and it would start attacking the same, both chemically and mechanically. In the presence, however, of the second sub-layer 244, it will start attacking, also chemically and mechanically, said second sub-layer 246, releasing the quantum failure identifiers 236', which in turn are detected by the operator in the exiting slag (38 in FIG. 2). When the operator detects the identifiers, depending on the quantity of identifiers, the frequency of their occurrence in the slag and the like may decide to either re-establish the solid status of the third sub-layer 222, or remove substantially all the slag, re-establish a good second layer 246, as well as a third 222 and fourth sub-layers as described above, and start the operation of the kiln again by feeding waste and/or additives to maintain the system in good condition.

In the case of this embodiment, the main thrust is to avoid substantially completely any attack of the modular refractory first sub-layer.

For additional assurance, quantum failure identifiers may also be embedded in the modular refractory first sub-layer 220, as described in the previous embodiment, so that failure of the brick may also be detected, if such a failure occurs for any reason at all. In such a case, it is preferable to have a different type of identifier in the first sub-layer 220 than in the second sub-layer 246 for better distinguishing the location of failure.

It is worth noting that in a different embodiment, quantum failure identifiers in the form of a plurality of discrete pieces, preferably selected from the group consisting of pebbles, gravel and china chips, may be distributed also within the substantially granular phase of modular refractory first sub-layer. These discrete pieces should have similar properties and behavior as described hereinabove for the discrete pieces included in the second sub-layer.

The operation of this embodiment is substantially the same as the operation of the previous embodiments, and it does not need further explanations.

Figure 5:
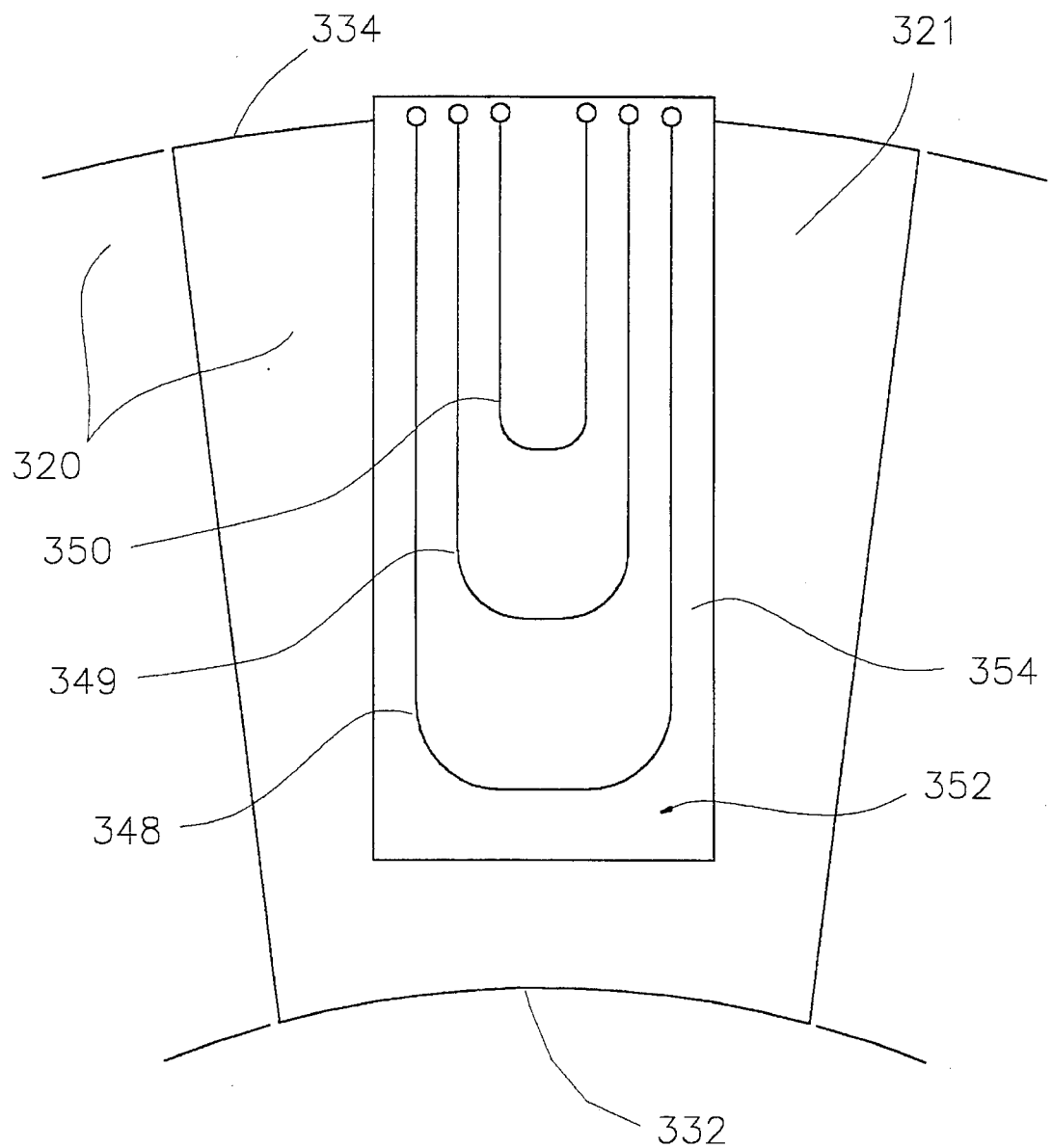
FIG. 5 shows a schematic cross sectional view of a brick of the modular refractory first sub-layer according to a different preferred embodiment of the instant invention, wherein the quantum failure identifiers are in the form of a plurality of electrical conductors.
Figure 6:
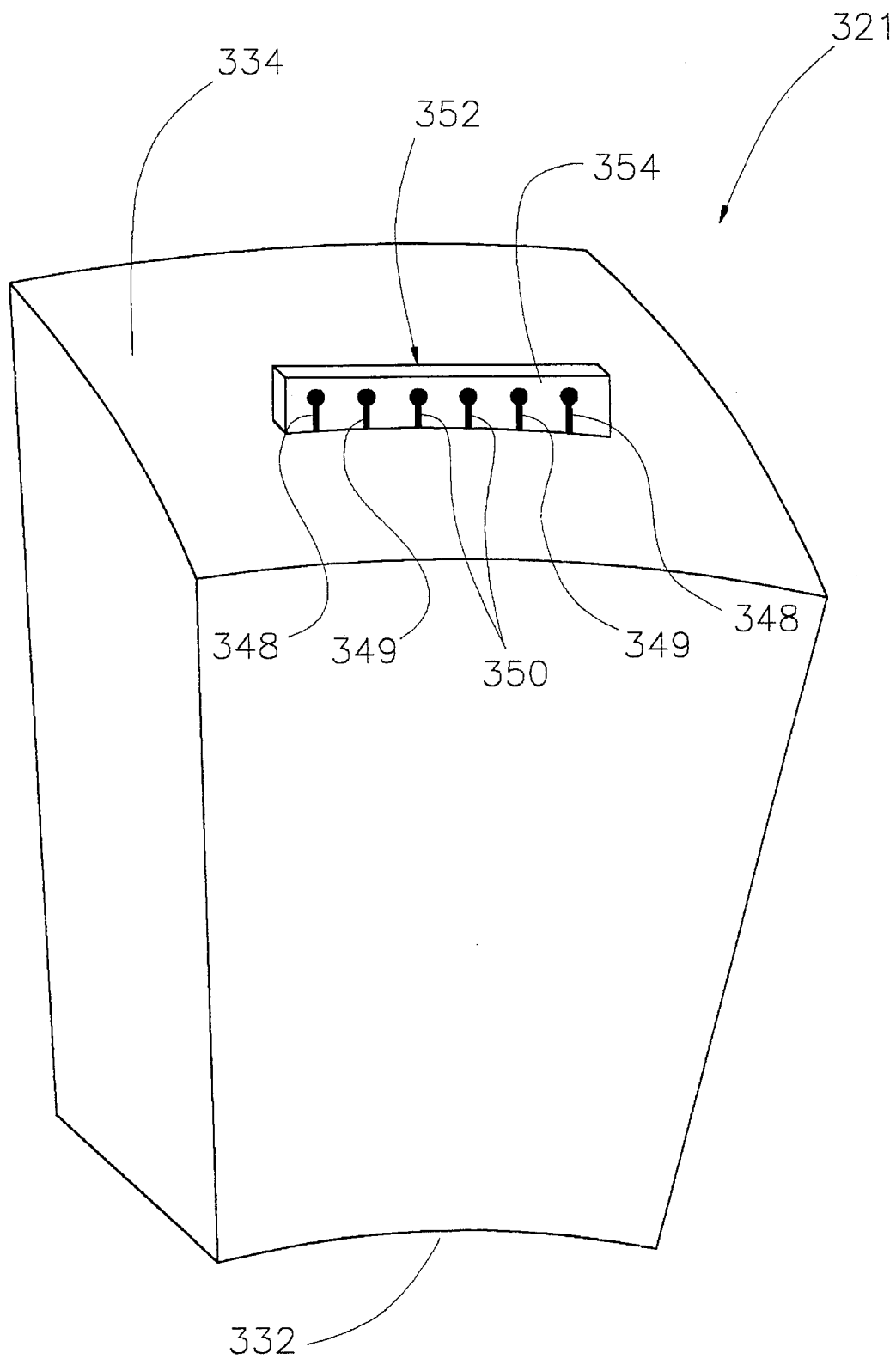
FIG. 6 shows a schematic perspective view of the brick of the embodiment of FIG. 5.
Figure 7:
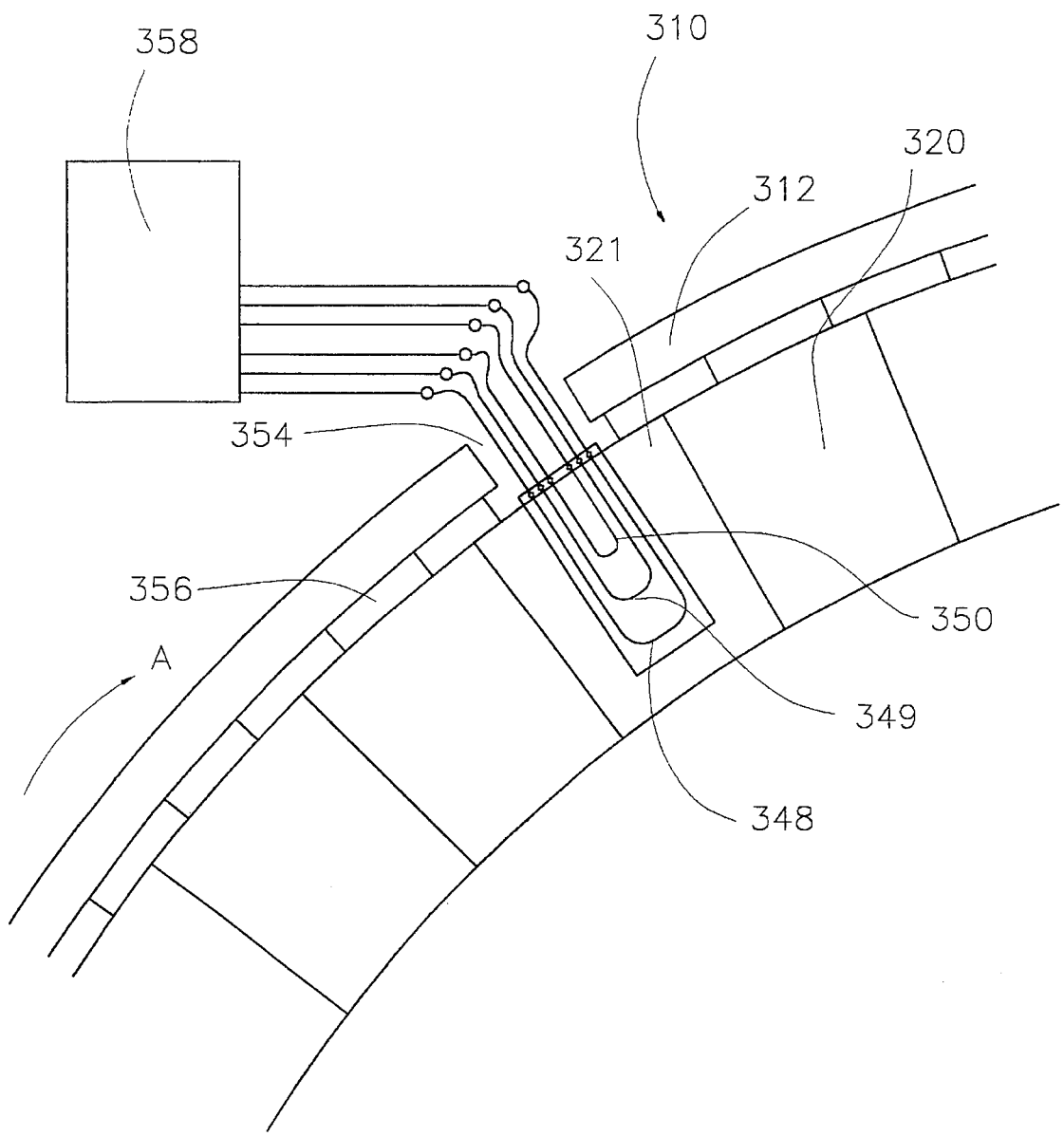
FIG. 7 shows a schematic fragmental cross sectional view of a kiln comprising a refractory brick of the embodiment of FIGS. 5 and 6.

In still a different embodiment of the instant invention, better illustrated in FIGS. 5 to 7, there is provided a plurality of electrical conductors forming U-loops 348, 349, and 350, for example, encased in the modular refractory first sub-layer 320, and more specifically, in a single refractory brick 321. FIG. 5 shows a cross section of the single brick 321, FIG. 6 is a perspective view of brick 321, while FIG. 7 represents a fragmental view of a cross section of the kiln 310, including the cross-sectional view of the refractory brick 321.

The electrical conductor U-loops 348, 349, and 350 may be in a wire form, or they may be part of a printed circuit 352, which circuit comprises a substrate 354 on which the conductor U-loops 348, 349, and 350 have been printed by well known to the art techniques. It is preferable that the conductors are made of high melting point metal, such as tungsten, for example. Lower melting point materials may also be used, however, since there is a considerable temperature gradient through the thickness of the brick, which protects the conductors from melting prematurely. The substrate 352 is preferably made of sintered alumina, such as the one used commonly for printed circuits, for example.

The electrical conductors 348, 349, and 350, whether in the form of wires or in the form of a printed circuit, are embedded in one or more refractory bricks 321. They are isolated from each other, and electrically insulated as embedded in the refractory, which is a good electrical insulator. They form U-loops toward the inside face 332 of the brick 321, while they extend through the outside face 334 of the brick 321, and they are available for electrical connections. Any reasonable number of electrical conductors may be used for the purposes of this embodiment of the instant invention. Preferably one to six, more preferably two to 4, and even more preferably 3 conductors are used looping at different intervals between the inner face 332 and the outer face 334, such as for example shown in FIGS. 5–7. The U-loops may be arranged to be one inside the other, As shown in FIGS. 5–7, or they may be arranged to be located side by side, or both. Other arrangements conforming to the requirements set forth in the description are within the scope of the instant invention.

Refractory bricks, similar to brick 321, are placed in locations of the first sub-layer 320 of the kiln 310, which are suspected to be prone to premature wear and/or failure. In such locations, holes 354 are made through the outer shell 312, and through a thermal insulation refractory 356, which is usually present in rotary slagging kilns, as already mentioned.

The electrical conductor loops 348, 349, and 350 are electrically connected to a continuity sensing monitor 358, which is adaptable to take action when the continuity of any conductor loop is interrupted by well known to the art techniques. Examples of such action are activation of a siren, automatic lowering of the temperature in the kiln, automatic cooling of the outer shell of the kiln, shutting off or turning on other devices helpful to prevent further damage to the refractory first sub-layer 320, and the like.

The monitor 358 may be hard wired to the conductor loops 348, 349, and 350, and be turning along with the kiln. In such a case, it is preferable that it is thermally insulated from the heat of the outer shell 312 by well known to the art techniques. It is also preferable that it is connected to other stationary equipment by wireless communication, also by well known to the art techniques.

It is also possible for the monitor 358 to be stationary, and establish momentary connection through contact points on the kiln and on the monitor, which contact points are adaptable to come together and establish the momentary connection once in every full revolution. It is further possible to use sliding contact points on the stationary monitor and full continuous contacts around the periphery of the rotating kiln for continuous communication between the two. Both these techniques are well known to the art, and they are broadly used for establishing connections between sliding brushes on peripheral contacts in different types of electrical motors.

In operation of this embodiment, the kiln is initially being operated, for example, in any number of ways already discussed. It is inevitable that at some point in time, the modular refractory 320 starts deteriorating, and its thickness starts decreasing until the loop of conductor 348 is reached. At this point, the harsh environment prevailing in the kiln disrupts the continuity of the conductor 348 by tearing apart the part of the exposed conductor. The continuity monitor detects in turn the breakage of continuity of the loop 348, and reacts by turning on a siren, for example, to notify the operator of the kiln that the thickness of the refractory 120 at that location has been reduced by the depth at which the loop of conductor 348 was encased away from the inside face 332 of the brick 321. The operator may then take suitable measures to reduce the progress of deterioration. The same process is applicable for the refractory deterioration to disrupt next the continuity of the conductor 349, and later of the conductor 350. When the operator is alerted by the monitor 358 that the deterioration of the refractory has reached the depth of conductor 350, the operator will still have some time to schedule an orderly shut down and re-bricking of the kiln, instead of confronting an unexpected catastrophic brick failure, which would most probably occur in the absence of the devices and methods of the present invention.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. These combinations also lie within the realm of the present invention. Furthermore, any attempted explanations in the discussion are only speculative and are not intended to narrow the limits of this invention.

In the different figures of the drawing, numerals differing by 100 represent elements which are either substantially the same or perform the same function. Therefore, in the case that one element has been defined once in a certain embodiment, its re-definition in other embodiments illustrated in the figures by the same numerals or numerals differing by 100 is not necessary, and it has been often omitted in the above description for purposes of brevity and clarity.

What is claimed is:

1. An incineration kiln device of the slagging type comprising:

an outer metal shell having an inside surface and an outside surface;

a protective layer comprising a first sub-layer adjacent to the inside surface of the outer metal shell, a second sub-layer on top of the first sub-layer, the second sub-layer comprising a substantially continuous phase, a third sub-layer comprising solidified slag, suitable to accept a fourth sub-layer of molten slag on top of it;

a quantum failure identifier at least partially encased within the substantially continuous phase, discrete pieces of the quantum failure identifier being lighter in color than the slag; and means for monitoring the quantum failure identifiers in slag exiting the kiln, in case at least part of said identifiers are transferred from the second sub-layer to the molten slag of the fourth layer during the operation of the kiln.

2. A device as defined in claim 1, wherein the first sub-layer comprises modular refractory.

3. A device as defined in claim 1, wherein the discrete pieces have a high enough melting point to substantially retain their shape and size for at least 1 hour when subjected to molten slag conditions prevailing during operation of the kiln.

4. A device as defined in claim 1, wherein the average particle size of the quantum failure identifier is in the range of 0.5 to 4 cm.

5. A device as defined in claim 4, wherein the average particle size of the quantum failure identifier is in the range of 1 to 2 cm.

6. A device as defined in claim 1, wherein the substantially continuous phase has a melting point between 2,300° and 3,000° F.

7. A device as defined in claim 1, wherein the discrete pieces of the quantum failure identifier have a melting point higher than a point at which the slag melts.

8. A device as defined in claim 1, wherein the discrete particles of the quantum failure identifier comprise discrete pieces selected from the group consisting substantially of gravel, pebbles, and a mixture thereof.

9. A device as defined in claim 1, wherein the discrete particles of the quantum failure identifier comprise china chips.

10. A method of protecting the integrity of an incineration kiln of the slagging type, the kiln comprising an outer metal shell having an inside surface and an outside surface, and a protective layer comprising a first sub-layer adjacent to the inside surface of the outer metal shell, and a second sub-layer on top of the first sub-layer, the second sub-layer comprising a substantially continuous phase;

the method comprising the steps of encasing a quantum failure identifier at least partially within the second sub-layer in the form of discrete pieces dispersed in said substantially continuous phase, the discrete pieces of the quantum failure identifier being lighter in color than slag exiting the kiln.

slagging the kiln, monitoring the quantum failure identifier in the exiting slag to determine whether there is presence of said quantum failure identifier indicating at least partial failure of the protective layer, and taking corrective action to restore the protective layer.

11. A method as defined in claim 10, wherein the discrete pieces have a high enough melting point to substantially retain their shape and size for at least 1 hour when subjected to molten slag conditions prevailing during operation of the kiln.

12. A method as defined in claim 10, wherein the average particle size of the quantum failure identifier is in the range of 0.5 to 4 cm.

13. A method as defined in claim 12, wherein the average particle size of the quantum failure identifier is in the range of 1 to 2 cm.

14. A method as defined in claim 10, wherein the substantially continuous phase has a melting point between 2,300° and 3,000° F.

15. A method as defined in claim 10, wherein the discrete pieces of the quantum failure identifier have a melting point higher than the melting point of the slag.

16. A method as defined in claim 10, wherein the protective layer further comprises a third sub-layer on top of the second sub-layer consisting substantially of solidified slag.

17. A method as defined in claim 10, wherein the protective layer further comprises a fourth sub-layer on top of the third sub-layer consisting substantially of molten slag.

18. A method as defined in claim 10, wherein the discrete particles of the quantum failure identifier comprise discrete pieces selected from the group consisting substantially of gravel, pebbles, and a mixture thereof.

19. A method as defined in claim 10, wherein the discrete particles of the quantum failure identifier comprise china chips.

* * * * *